(12) United States Patent
Sullivan et al.

(10) Patent No.: US 6,886,564 B2
(45) Date of Patent: May 3, 2005

(54) NASAL MASK WITH INTEGRAL MOULDABLE STRAPS

(75) Inventors: Colin E. Sullivan, New South Wales (AU); Paul Wilkie, New South Wales (AU)

(73) Assignee: Australian Centre for Advanced Medical Technology Ltd., New South Wales (AU)

( * ) Notice: Subject to any disclaimer, the term of this patent is extended or adjusted under 35 U.S.C. 154(b) by 82 days.

(21) Appl. No.: 10/332,801

(22) PCT Filed: Jul. 16, 2001

(86) PCT No.: PCT/AU01/00860

§ 371 (c)(1),
(2), (4) Date: Feb. 13, 2003

(87) PCT Pub. No.: WO02/05883

PCT Pub. Date: Jan. 24, 2002

(65) Prior Publication Data

US 2003/0145857 A1 Aug. 7, 2003

(51) Int. Cl.[7] .............................................. A62B 18/08
(52) U.S. Cl. ............................. 128/206.24; 128/206.21
(58) Field of Search ....................... 128/205.25, 205.29, 128/206.11, 206.12, 206.13, 206.14, 206.18, 206.21, 206.23, 206.24, 206.25, 206.27, 206.28, 207.11, 207.13, 207.17

(56) References Cited

U.S. PATENT DOCUMENTS

| | | | | |
|---|---|---|---|---|
| 695,403 | A | * | 3/1902 | Longden ................ 128/206.12 |
| 2,348,287 | A | * | 5/1944 | Fiekers ........................ 156/108 |
| 2,634,725 | A | * | 4/1953 | Lo .......................... 128/206.19 |
| 4,520,509 | A | * | 6/1985 | Ward .............................. 2/206 |
| 4,790,307 | A | * | 12/1988 | Haber et al. ........... 128/206.19 |
| 4,827,923 | A | * | 5/1989 | Bishop et al. ......... 128/206.11 |
| 5,265,280 | A | * | 11/1993 | Walsh ........................ 128/206 |
| 5,570,689 | A | | 11/1996 | Starr et al. |
| D440,302 | S | * | 4/2001 | Wolfe ..................... D24/110.1 |
| 6,338,340 | B1 | * | 1/2002 | Finch et al. ........... 128/205.27 |
| 6,718,982 | B2 | * | 4/2004 | Smith et al. ........... 128/207.12 |
| 2004/0118405 | A1 | * | 6/2004 | Amante et al. ........ 128/206.19 |

FOREIGN PATENT DOCUMENTS

| | | |
|---|---|---|
| AU | A-32914/95 | 2/1996 |
| AU | 46837/97 | 7/1998 |
| GB | 2 262 891 A | 7/1993 |

OTHER PUBLICATIONS

DE 3840436 A; Laier–Groeneveld; Jun. 7, 1990; Derwent Abstract Accession No. 90–179610/24.

* cited by examiner

*Primary Examiner*—Henry Bennett
*Assistant Examiner*—Teena Mitchell
(74) *Attorney, Agent, or Firm*—Nixon & Vanderhye

(57) ABSTRACT

A mask for supplying gas under pressure to the nasal airway of a human includes a series of flexible stretchable straps formed from an elastomeric material for locating the mask against the human face. The straps are integrally formed or joined to define a perimeter enclosing an aperture adapted to fit around the nasal area of a human. The straps are configured to approximate to the three dimensional shape of the region around the nasal area of the human face as they arm stretched, to form a tight fitting seal. The mask may be used with or without a manifold.

27 Claims, 10 Drawing Sheets

NASAL MASK WITH INTEGRAL MOULDABLE STRAPS

FIELD OF THE INVENTION

This invention relates to a mask for supplying gases, typically fresh air or oxygen to the airways of humans.

BACKGROUND OF THE INVENTION

Various different types of masks are used to provide fresh air or oxygen to the airways of humans. A specialised category of masks is used to provide positive pressure to the human airway. Positive pressure applied in this manner has two different goals.

In a first category, positive pressure is applied to the lungs for the purpose of stabilising the lungs, and in particular for maintaining a minimum inflation level of the small air spaces in which gas transfer occurs (the alveoli). This therapy is very useful in patients with a variety of lung diseases, where the disease process tend to lead to collapse (closure of the airway containing regions of the lung).

In a second category, the positive pressure is applied to the nasal airway with the intention of maintaining the pressure in, and the patency of, the upper airway. This form of positive airway pressure is known as nasal continuous positive airway pressure (nasal CPAP). This is now the "gold standard" treatment for the condition known as obstructive sleep apnea (OSA), and also for snoring. Obstructive sleep apnea is a condition in which the upper airway closes in sleep, and does so repeatedly. Nasal CPAP, when applied for the duration of sleep, stabilises the upper airway and allows for normal sleep and normal breathing.

Masks for applying nasal CPAP, or nasal pressure support ventilation have a requirement to be able to deliver pressure and flow and maintain pressures within the mask without permitting leaks. Leaks are undesirable as they can allow the pressure in the mask to drop below a therapeutic level. Leaks may also be an irritation particularly, if the leak causes jets of air/oxygen to be directed into the patient's eye. Leaks interrupt a patient's sleep which is undesirable as interrupted sleep is known to be of much less value than uninterrupted sleep. Further, as the masks are for use during natural sleep, a high level of comfort in the fit of the mask is necessary.

One very common mask design includes three separate components as follows:
1. A soft mouldable rubberised interface which comes in direct contact with the patient's facial skin.
2. A rigid manifold to which the soft interface is connected, and which covers the patient's nose. The manifold includes:
   a) connector lugs to which straps from a harness are connected;
   b) connections to an air delivery pipe; and
   c) a number of relatively small holes or equivalent feature to provide a controlled leak of air to the atmosphere.
3. A harness which goes around the head from which three or more straps extend to connect to the lugs on the rigid manifold.

A seal is achieved by the mask being pulled onto the face by the straps attached to the rigid manifold. The seal is achieved by the rim of the mask coming into contact with the skin. In this way, direct force is applied via the straps (harnessed place around the head), and transmitted through the rigid manifold. There are a number of disadvantages with this mask which are discussed in more detail below following a description of other, known mask types.

More recently, in order to achieve a good seal "bubble" type gas delivery masks have been developed. One such mask is described in Australian Patent No. 643994, dated 16 May 1991. The mask described therein has a face contacting portion which is formed from an elastomeric material and is shaped to define a large bubble or dome shaped chamber. When gas is delivered through the chamber, the chamber tends to balloon outwardly and, when fitted to a patient, the face contacting portion is caused to overly a region of the patient's face and seal three dimensionally with the contours of the overlaid facial region. For practical reasons the mask is integrated with a rigid shell-like moulding which does not contact the patient's face. The shell is provided to enable a gas supply line to be connected to the mask, to facilitate fastening of the mask to a patient's face and to minimise the risk that movement of the gas supply line will disrupt the seal between the mask and the patient's face.

Other earlier masks comprise a shell custom moulded to fit around the individual nose for each patient, and either use a glue, or alternatively a soft inner part against which a tight fit is achieved. Once again, this type of mask may be held in place by straps and a head harness attached to the hard shell.

The main problems when designing a mask is that the mask must be able to achieve an air tight seal with the subject's face and at the same time be sufficiently comfortable to be able to be worn for hours without causing discomfort to the subject and in particular to allow the subject to sleep.

Movement of the head, and subsequent dislodgment of the mask, and breakage of the seal are major problems with prior art masks. This is a particular problem when a patient lies on their side, with the side of their head on the pillow as the rigid manifold tends to contact the pillow The contact moves the manifold relative to the patient's face, is transmitted to, and affects the integrity of the seal and also the manifold can be pushed onto the patient's nose causing discomfort to the patient.

Using the first type of mask as described above, which includes the three separate components, seal breakage is addressed by pulling the straps firm. This however, can lead to discomfort for the patient.

In the second mask type described above (the "bubble type mask"), the bubble provides a continuous rolling seal, so that minor head and other movements are accommodated within the excess thin membrane. However, large head movements may not be accommodated by the rolling seal.

A major problem for all masks is that an air delivery pipe must be attached to the mask at some point. Movement of the head and the pipe leads to torsion which is transmitted through the hard shell of the manifold and can cause the sealing margins of the mask to rise up and allow a leak. The above-referenced "bubble mask" patent, (Australian patent No 634994), tries to address this by having a "universal joint" between the air delivery pipe and the rigid manifold. Australian Patent No 684412, by the same inventor as the earlier Australian patent No 634994, addresses this problem by making a portion of the wall containing the gas supply port exhibit a degree of flexibility that is greater than that of adjacent regions of the mask so that movement by the connecting gas supply line will be accommodated at least in part by flexing of the wall portion. Whilst both masks produce relatively satisfactory seals they are quite bulky, relatively heavy and ungainly.

In existing masks, because the straps must anchor onto a rigid point, they are attached to the rigid manifold; the result is that typically the strap leaves the side of the face near the cheeks, and passes through air until it reaches the lug on the manifold. This "floating" part of the strap, provides a significant weakness and adversely affects the integrity of the seal when the patient's head moves When the subject rolls onto their side, this floating part of the strap is easily distorted, and pulls on the mask and leads to a leak.

In one aspect, the present invention seeks to provide an improved mask which reduces the relative size, weight and bulk of the existing masks and yet provides a satisfactory seal.

A variant of the mask may be used to supply treated air, oxygen or an air/oxygen blend or the like to patients. In a known technique such treated air is supplied from a pipe located near a patient's nasal airway and the flow of air is directed past the patient's nares. Thus, in a related aspect the present invention seeks also to provide harness for supporting a pipe for supplying a flow of gas to a patients nasal airway.

SUMMARY OF THE INVENTION

Thus in a first broad aspect of the present invention, there is provided a mask for supplying gas under pressure to the nasal airway of a human, including:

a series of flexible stretchable straps formed from an elastomeric material for locating the mask against the human face, the straps being integrally formed or joined to define a perimeter enclosing an aperture adapted to fit around the nasal area of a human, the straps being shaped and configured to approximate to the three dimensional shape of the region around the nasal area of the human face; and a manifold disposed on the non-face contacting side of the face contacting portion, the manifold including means for connection to a gas supply means;

the arrangement being such that stretching of the straps around the nasal area of the human causes the straps to mould to the contours of the nasal area of the face so that the straps form a seal around the nasal area which is a relatively tight fitting seal.

In the present invention instead of providing a separate sealing membrane and support shell, the straps themselves provide the seal. This greatly reduces the size and weight of the mask. The patient's nose extends into the manifold. The straps closely fit to the patient's face and the problems of flexing due to the connection with the air delivery pipe are reduced.

Straps for attachment to a head harness are used to define, locate and provide a seal around the perimeter of a patient's nose. Because the straps are sufficiently flexible they can mould around the perimeter, and in doing so, as the mask stretches around the margins a tight fitting comfortable seal is achieved.

The mask of the present invention, allows the straps to pass over the patient's cheeks, rather than "extending" through air down the side of their heads. This provides a more secure fit of the mask and makes the mask less likely to move.

The aperture may be generally triangular.

The mask may further include a flexible sealing element extending along one inwardly facing side of each strap. The sealing element may be generally convex.

In one embodiment, a channel extends around the perimeter in which an adhesive means (such as "DuoDerm" or Elastogel") for sealably adhering the perimeter to the human facial area and minimising leakage, is provided It is a significant advantage of the present invention that the mask can be made in fewer parts than the mask of AU 684412, typically only two, with the straps and sealing element moulded in one part and the manifold in second part, which can make manufacture of the mask simpler and cheaper.

Typically, three flexible arms extends away from the straps for securing the face-contacting portion to a patient's head or face.

It is preferred that a pad is defined at the end of each flexible arm distal from the plate. The pad may define slots so as to be connectable to harness straps attached to a cap. These harness straps could be connected to the pads by fastening materials such as velcro or the like In a particularly preferred embodiment, the pads, straps and sealing element are all integrally moulded from an elastomeric material, typically a high tear resistant silicone elastomer such as Silastic (Registered Trade mark of the Dow Corning Corporation) or Santoprene (Registered Trade Mark of Monsanto Co). The thickness of the straps is typically between 2 to 4 mm.

Typically, a number of small holes will be defined on the manifold to provide a constant leak to atmosphere and thus a way out for expired air. The number and size of the holes are determined by the pressure of air supplied to the mask and flow delivery system and are chosen to enable the desired pressure and air flow through the mask.

In a particularly preferred embodiment, part of the manifold extends along one of the arms of the mask, typically the arm which extends from the top of the mask where an air port or hole for receiving a gas delivery pipe is provided.

The provision of the air port at the end of one of the arms of the mask greatly reduces the torsion effects on the mask due to the air delivery pipe.

The manifold is typically made of the same thin flexible elastomeric material that is used for the straps. Typically, the material forming the manifold is about 1 mm thick.

The manifold should ideally be somewhat larger than a typical human nose. In this manner when a person lies on their side with the side of their head on a pillow, movement of the head can be accommodated by flexing and compression of the manifold. Because the manifold is soft and flexible, this movement is not transmitted to the seal but is largely absorbed by flexing of the manifold. Also because the manifold is flexible, any contact of the manifold with a patient's nose should not cause discomfort to the patient.

In one particularly preferred embodiment, the mask includes a harness and an air pipe extending to a junction port attachable to the top of a patient's head and an air delivery pipe is rotatably mounted to that junction port, thus allowing a patient's head to turn without moving the air delivery pipe.

The present invention also encompasses a method of supplying gas to the airway of a human using any of the aspects or embodiments of the invention described above.

Typically the method will be used to supply oxygen or air to the airway for nasal CPAP, or nasal ventilation or nasal pressure support.

However, in a related aspect a variant of the mask may be used to supply treated air, oxygen or an air/oxygen blend or the like to patients wherein the mask is open or merely acts as a harness or anchor for air pipes for directing a flow of air past the patients nares and for creating a zone of clean air around a patient's nares.

Thus in a second aspect of the present invention there is provided a harness for supplying gas under pressure to the nasal airway of a human, including:

a series of flexible stretchable straps formed from an elastomeric material for locating the harness against the human face, the straps being integrally formed or joined to define a perimeter enclosing an aperture adapted to fit around the nasal area of a human, the straps being shaped and configured to approximate to the throe dimensional shape of the region around the nasal area of the human face; and a means for supplying a flow of gas directed generally towards the perimeter of the harness including means for connection to a gas supply means;

the arrangement being such that stretching of the straps around the nasal area of the human causes the straps to mould to the contours of the nasal area of the face so that the straps anchor the harness to the human face relatively tightly.

BRIEF DESCRIPTION OF THE DRAWINGS

The invention will now be described by way of example only and with reference to the accompanying drawings in which:.

DETAILED DESCRIPTION OF A PREFERRED EMBODIMENT

Figure 1:
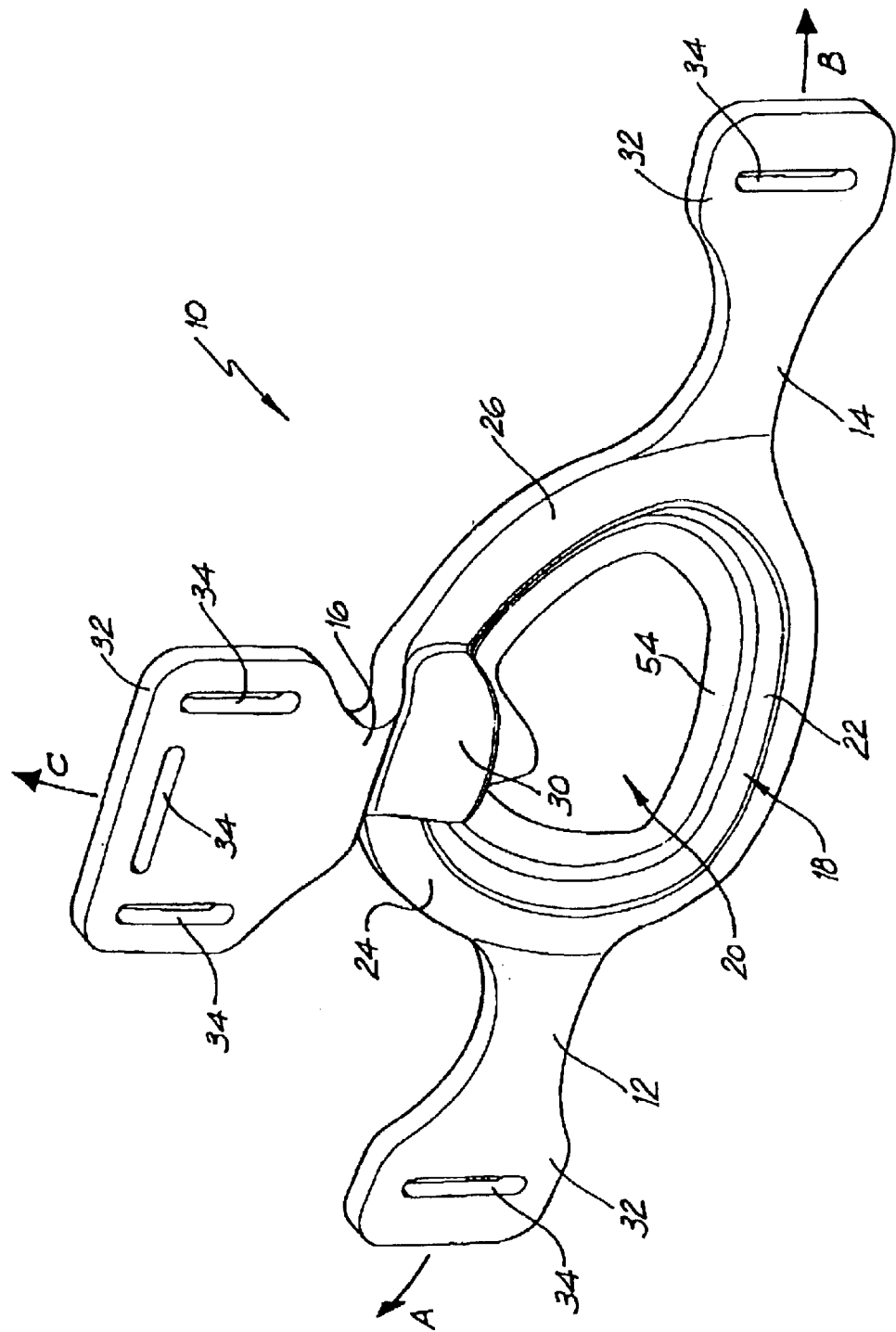
FIG. 1 is an isometric view of a mask embodying the present invention, but without a manifold.

Referring to the drawings, FIG. 1 shows a part 10 of a mask. The mask includes three straps, 12, 14, 16 which are integrally moulded with a generally triangular face engaging portion or perimeter 18 enclosing a generally triangular aperture 20. The straps can be considered to be an extension of members defining the perimeter as the straps 12, 14, 16 are integrally formed and connected via the perimeter. Thus straps 12 and 14 are connected via perimeter member 22, and pulling on the ends of straps 12 and 14 also stretches perimeter member 22. Likewise, straps 12 and 16 are integrally formed and connected by perimeter member 24, and straps 16 and 14 by perimeter member 26. The perimeter 18 is integrally formed with the straps from a flexible stretchable elastomeric material (such as Silastic or Santoprene) and when the straps are stretched in a direction as shown by the arrows A, B and C, then the face engaging portion perimeter stretches also and the aperture 20 enlarges slightly.

Figure 2:
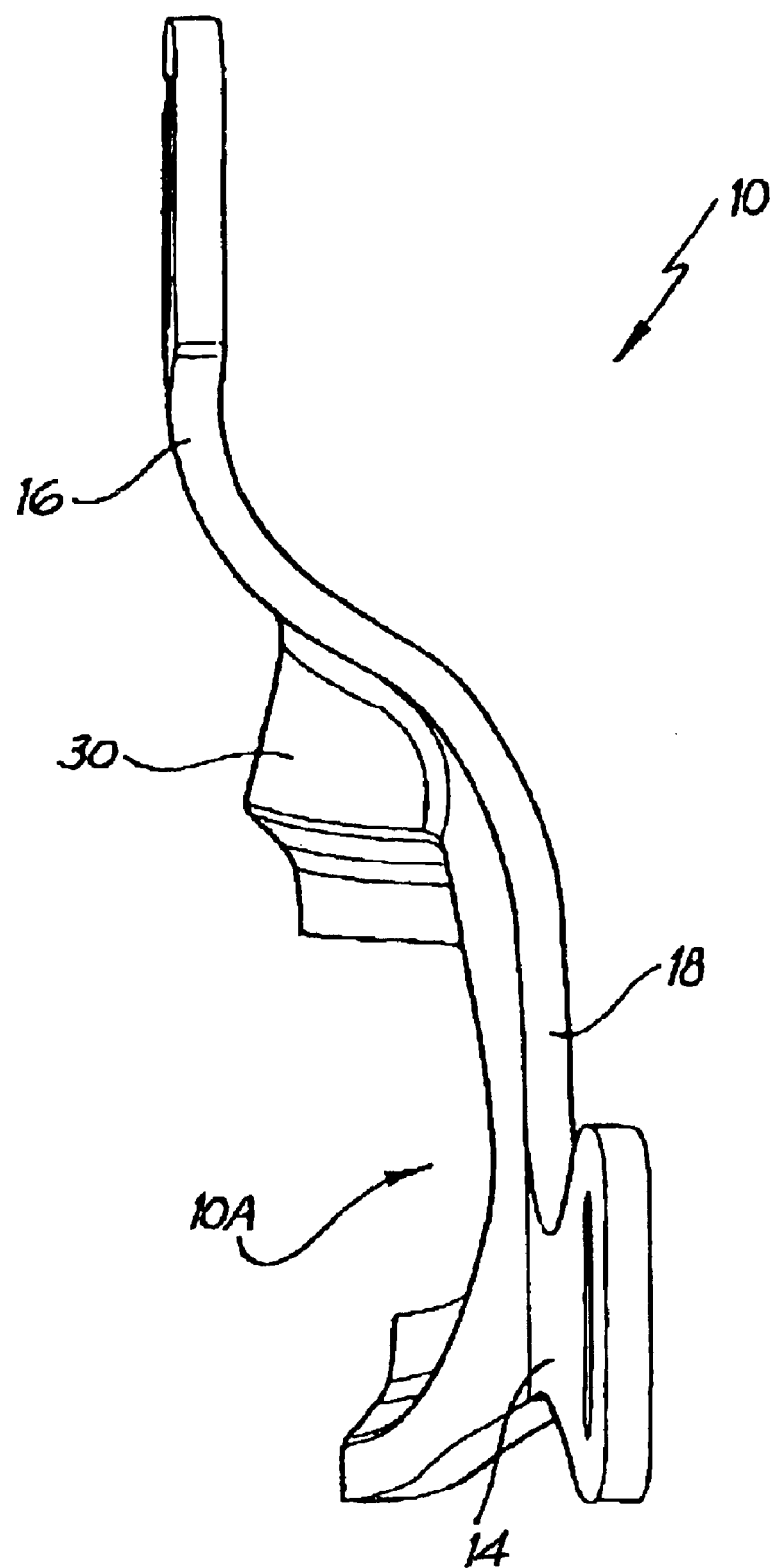
FIG. 2 is a side view of the mask shown in FIG. 1.
Figure 3:
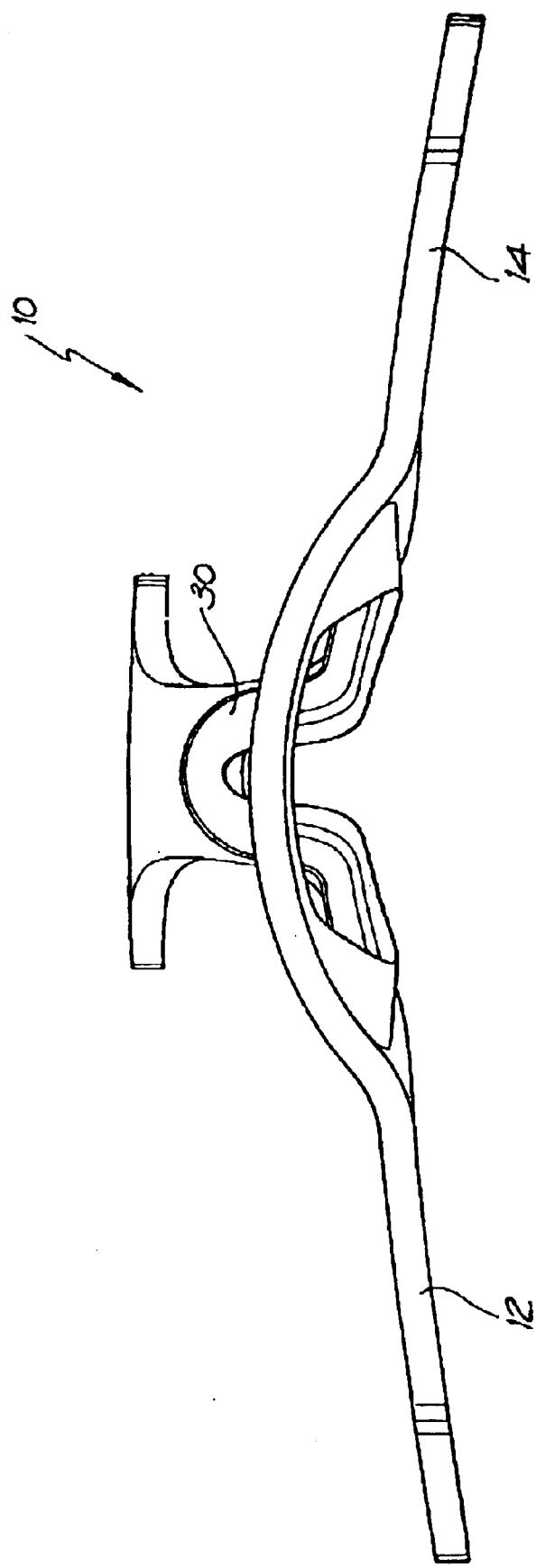
FIG. 3 is a bottom plan view of the mask shown in FIG. 1.

As can be seen in FIGS. 2 and 3, the face engaging portion 18 of the mask and the straps themselves, particularly the top strap 16, are moulded so that they tend to approximate to the contours of a human face. Thus the upper part of the face engaging portion includes a generally concave portion 30 which fits tightly over the bridge of a patient's nose.

The ends of the straps define pads 32 which include slots 34 for attachment to a harness (not shown) which fits around the back of a person's head for stretching the mask over a person's nose. The straps and perimeter may be between 2 mm to 4 mm thick.

Figure 4:
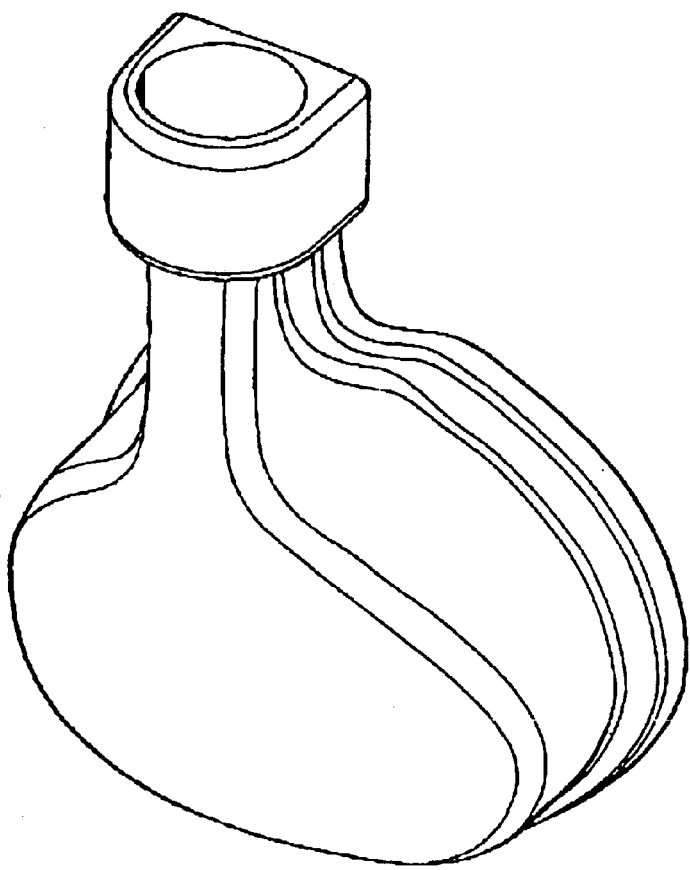
FIG. 4 is an isometric view of a manifold for the mask shown in FIGS. 1 to 3.
Figure 5:
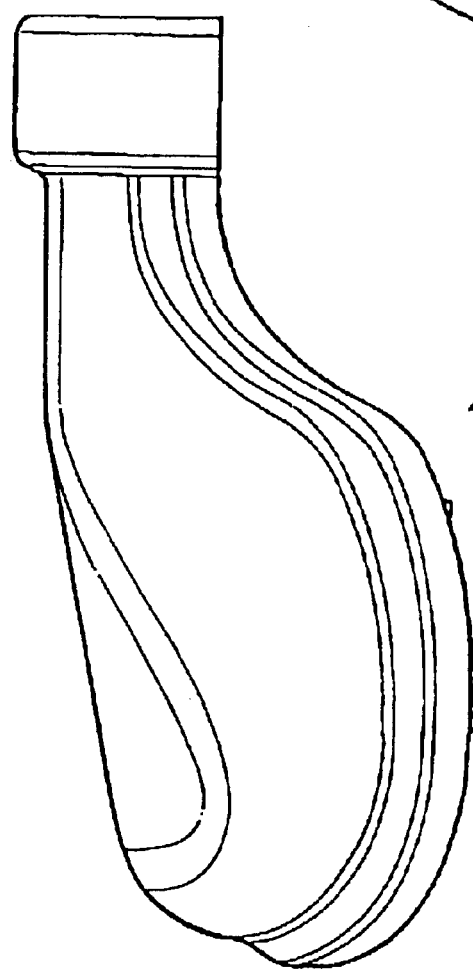
FIG. 5 is a side view of the manifold shown in FIG. 4.
Figure 6:
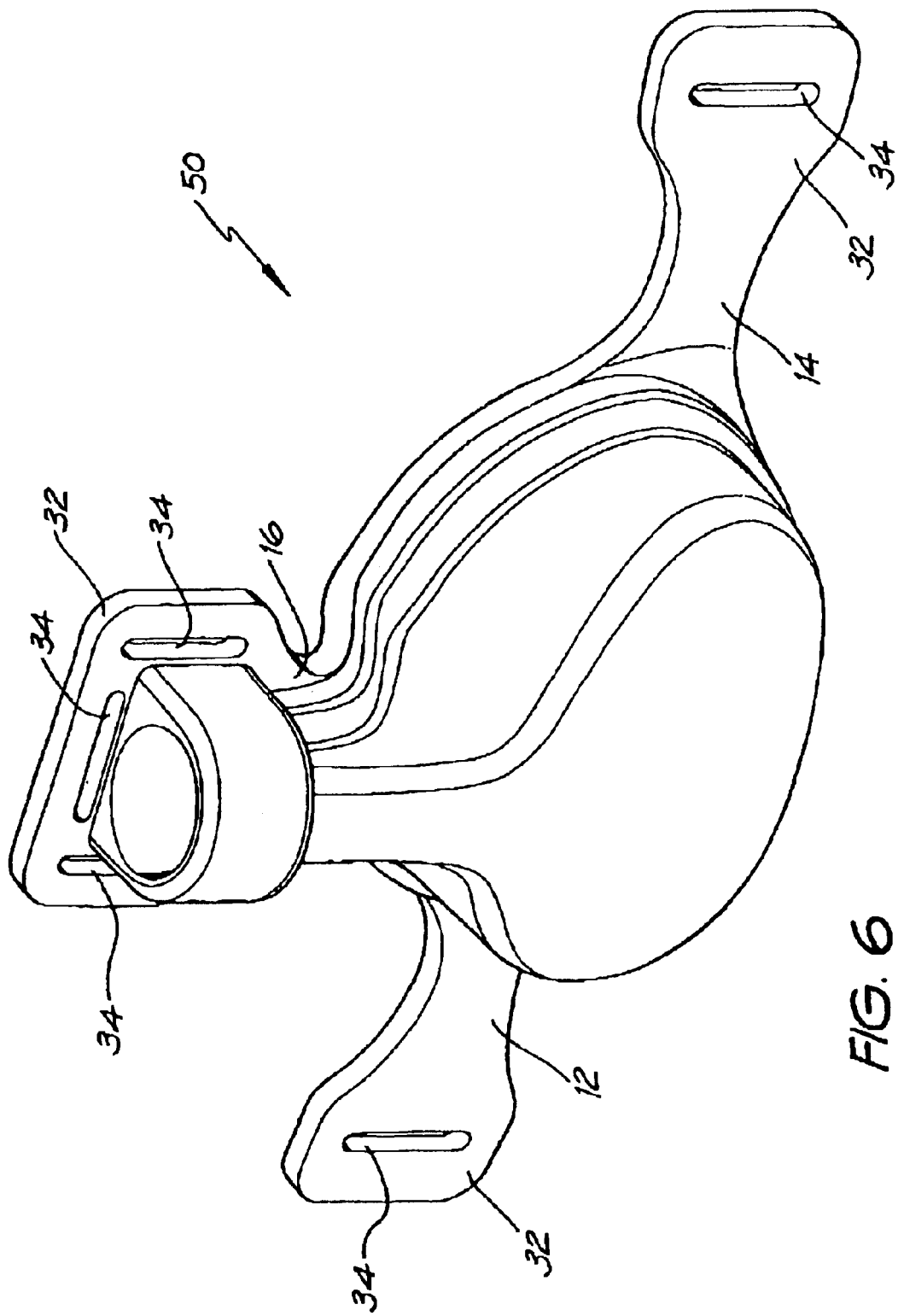
FIG. 6 is an isometric view of a complete mask combining the mask of FIGS. 1 to 3 and the manifold of FIGS. 4 and 5.
Figure 7:
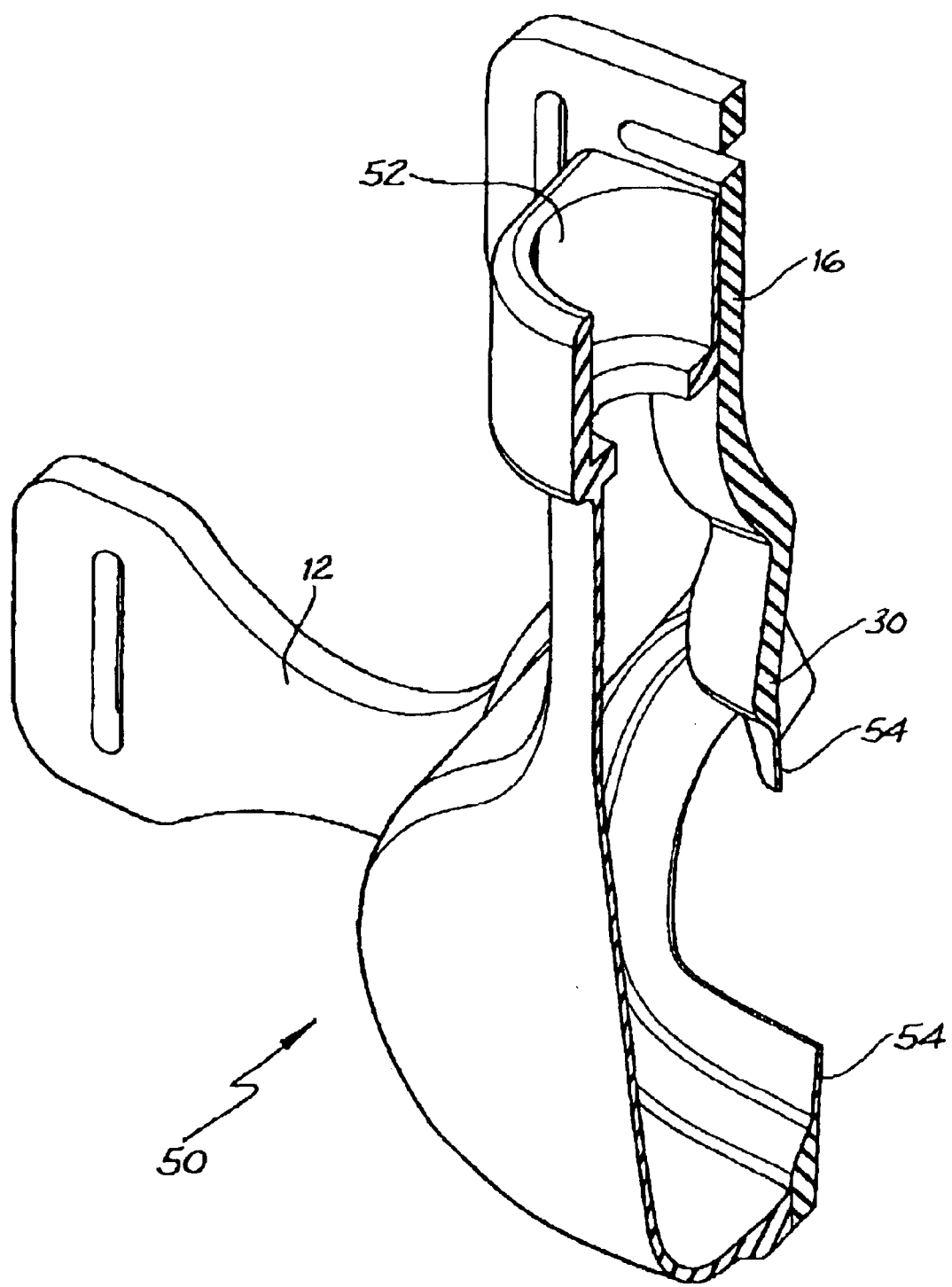
FIG. 7 is a section through the mask of FIG. 6.

FIGS. 4 and 5 illustrate a manifold 40 which defines an open face 42 which defines an open face 42 which sealingly mates with the non-face engaging side 10A of the mask 10 and the two components 10 and 40 may be glued or otherwise fixed together to form a complete mask 50 as shown in FIGS. 6 and 7. The manifold is flexible and compressible in contrast with the prior art, allowing movement of a patient's head lying side-on on a pillow, to be accommodated by compression or deformation of the manifold. As is best seen in FIG. 7, an air port 52 for connection to an air delivery pipe is located at a distal end of the strap 16 remote from the aperture 10.

Around the inside of the perimeter 18, there is an additional thinner, more flexible sealing element 54 best seen in FIG. 7. This membrane may be 1 mm thick or less.

The principal of operation of the mask is similar to that of pulling on a tight fitting garment. The nose and its surrounds could be considered to be a cone and the perimeter 18 is an elastic funnel shaped to approximate to the cone yet with slightly smaller margins and an open central region. As it is pulled over the cone, as the straps 12, 14, 16 are tightened, the inner margins of the funnel contact the surface of the cone and then stretch around it causing a closed seal. The margins of the mask are the perimeter members. As these members stretch, they pull inwards to the skin on the face and are at all times in direct contact with the skin. This is in direct contrast to the operation of the straps in the conventional masks and the bubble type masks where the masks are attached to a lug on a rigid manifold and extend for a substantial distance in mid air, not in contact with a person's face, before they contact a person's face usually on the back of their cheek close to their ears.

Since, in the present invention, the straps are always in contact with the skin, this provides a much greater stability of the mask on the face. The straps also provide a seal having a large sealing or contact area. The additional thinner flexible sealing element 54 improves the seal provided by the stretching of the face engaging portion. However, it is not critical to the performance of the mask and could be omitted.

Figure 8:
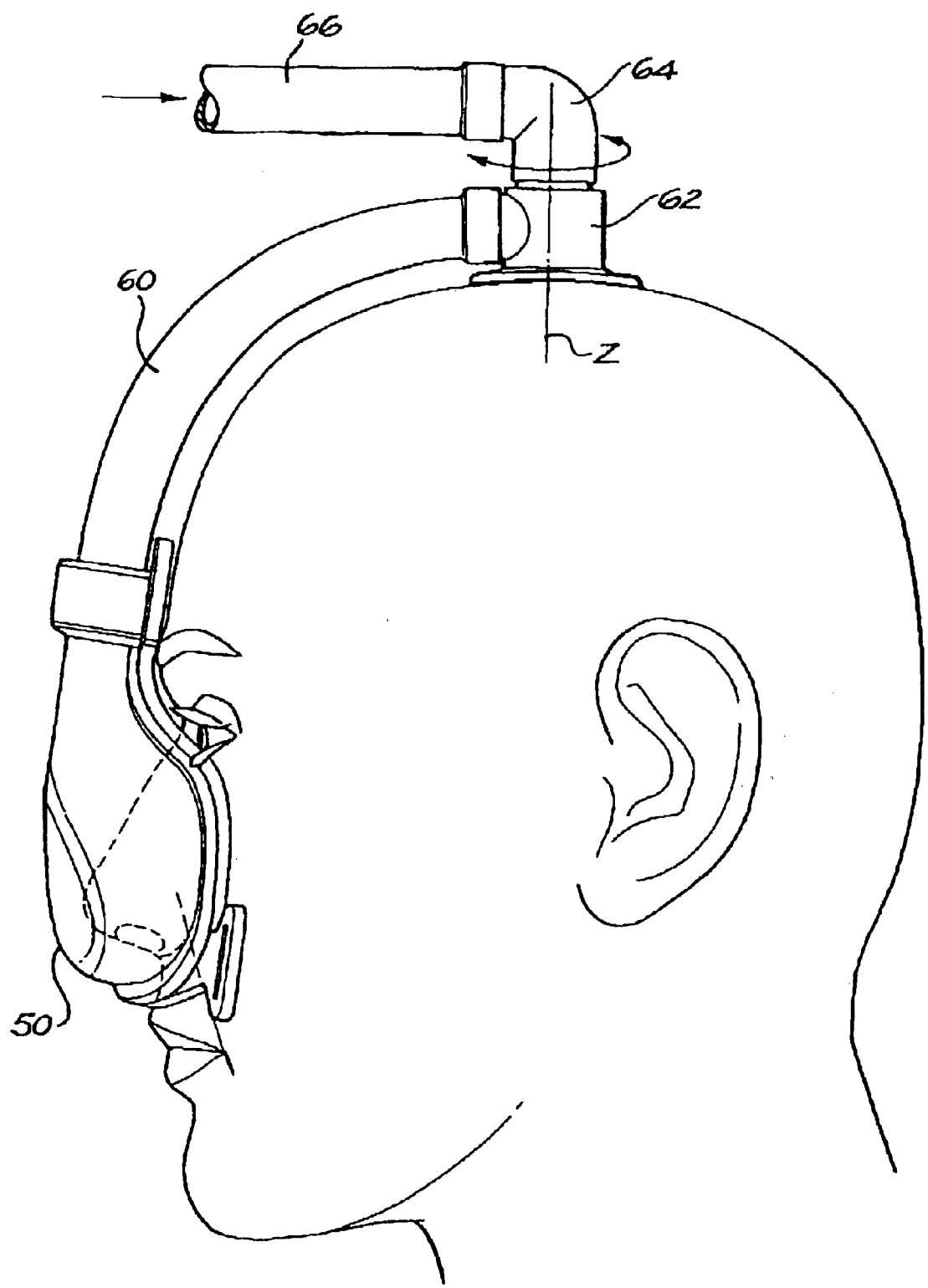
FIG. 8 is a schematic drawing illustrating a head mounted junction port for receiving an air delivery pipe.

FIG. 8 illustrates a variant of the invention where a short pipe 60, which may be an extension of the manifold and strap 16 extends to an air port junction 62 fixed to the top of a patient's head. An elbow pipe 64 is rotatably mounted in the air port junction 62 rotating about axis Z perpendicular to the top of the patient's head. The elbow 64 is connected to an air delivery pipe 66. With this arrangement, the patient's head can turn without being affected or affecting delivery pipe 66.

In a yet further variant, additional slots 34 are provided in the pads 32 of the arms 12 and 14 to receive the ends of a chin strap.

Figure 9:
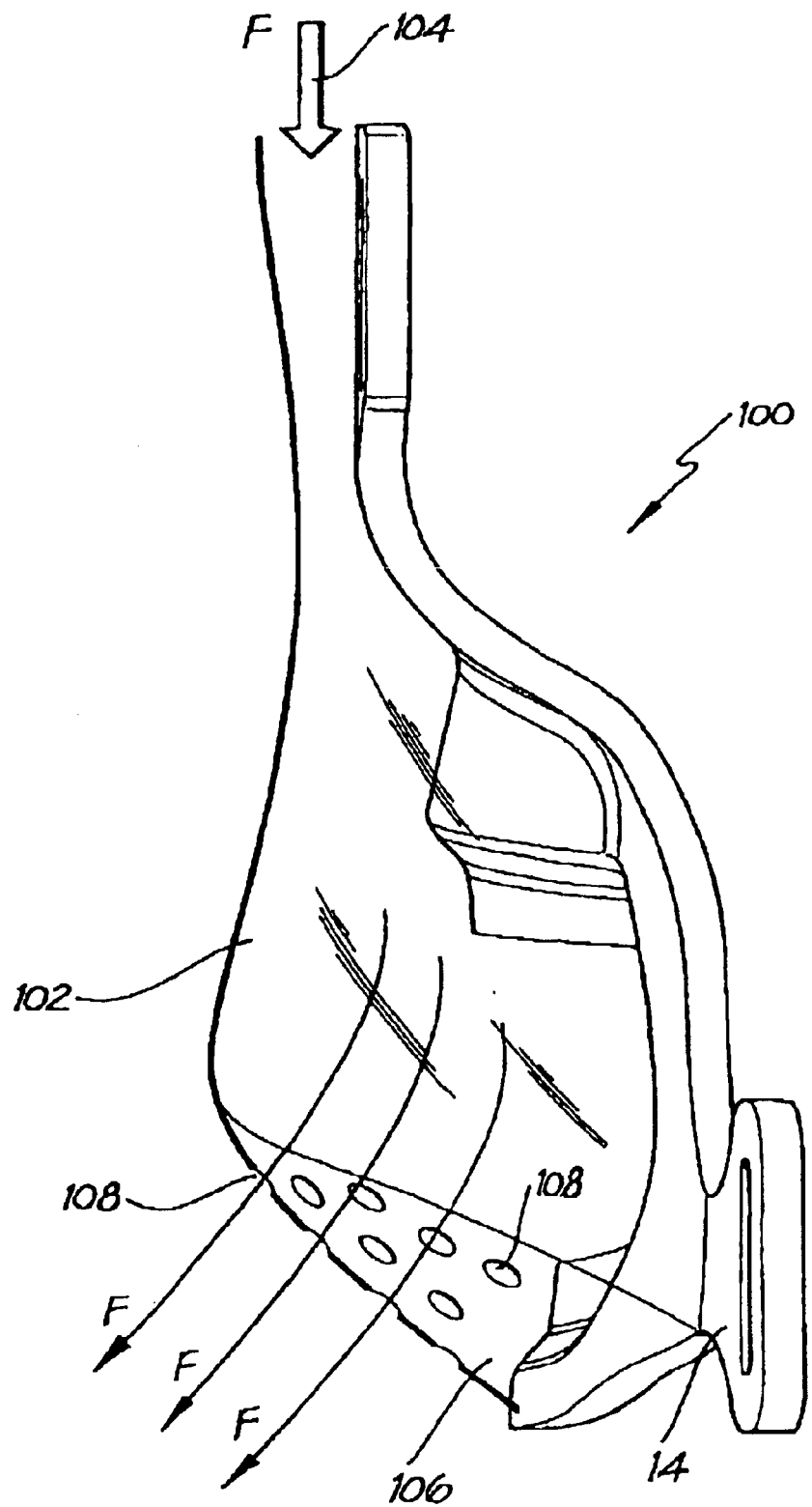
FIG. 9 shows a variant of the mask of FIG. 6.

FIG. 9 illustrates a variant 100 of the mask of FIG. 6. The mask of FIG. 9 is used for supplying clean filtered air, treated air, or an air/oxygen blend to a patient where it is not necessary or desirable for the patient to wear a closed mask enclosing the patient's nose. Closed masks tend to uncomfortable when worn for long periods of time. Further if humid air is supplied by a closed mask to an asthma sufferer for example, water will tend to condense inside the closed mask which is undesirable. In this embodiment the manifold is replaced by a canopy or hood 102 which directs air under pressure 104 down the canopy towards the patient's nares. The base 106 of the canopy is open, being either totally open, or as illustrated in FIG. 9 defining a large number of relatively large diameter holes 108 typically having a diameter of about 5 mm to 10 mm or more. In use when the harness is worn the patient's nose is located under the canopy 102 and the patient's nares are adjacent the base 106 of the canopy, The straps which are always in contact with the skin this provide a very stable anchoring of the mask on the face. However in contrast with the mask of FIGS. 1 to 8, no seal is required. This arrangement allows a relatively high volume fast flow F of low pressure air past a patient's nares and creates an atmosphere around the nares which is dominated by the low pressure air or air/oxygen mix. The canopy is preferably transparent as shown in FIG. 9. The same effect may be created by simply forming a large number of relatively large diameter holes, say 5 to 10 mm or more in the base of manifold of the mask of FIG. 6.

Figure 10:
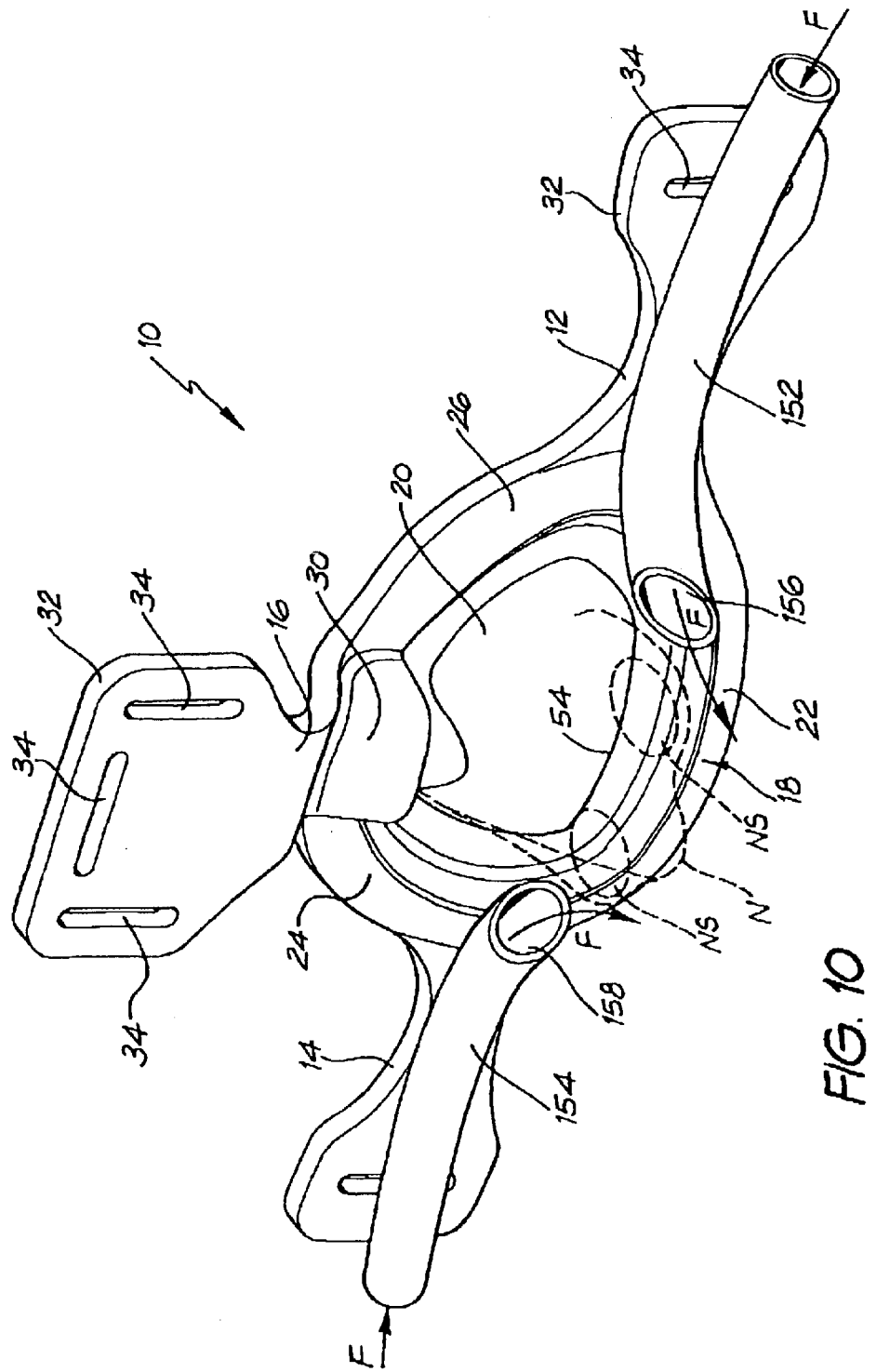
FIG. 10 shows an isometric view of a variant of the mask of FIG. 1.
Figure 11:
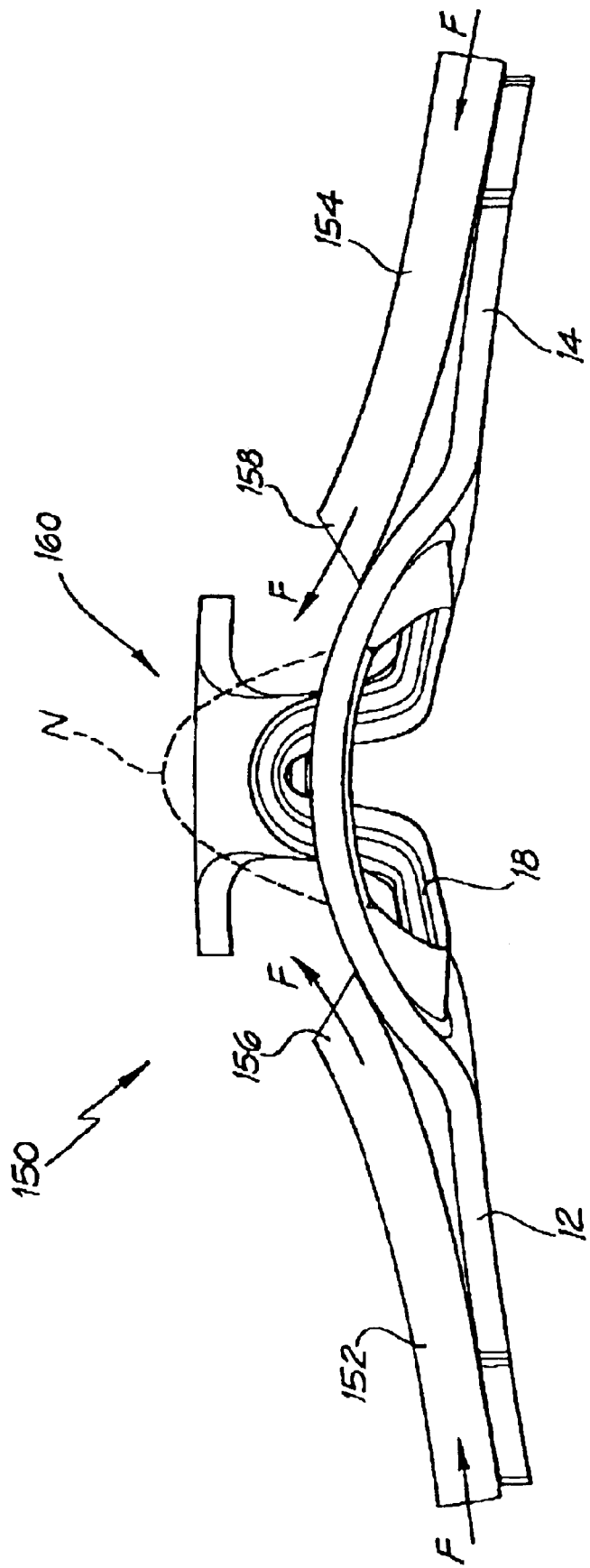
FIG. 11 shows an underneath plan view of the variant of FIG. 10.

In the embodiment of the mask/harness 150 shown in FIGS. 10 and 11, pipes 152, 154 extend along each of the straps 12, 14 respectively and terminate in open ends 156, 158 adjacent the perimeter 18 of the mask/harness. In use when the harness is worn the patient's nose extends through the perimeter 18. The straps which are always in contact with the skin provide a very stable anchoring of the mask on the face. Again in contrast with the mask of FIGS. 1 to 8, no seal is required. A flow of pressurised filtered clean air passes along the pipes 12 14 as shown by the arrows F. This flow creates a 'virtual space' or zone of clean filtered air around the patient's nose N and nares NS shown in dashed outline in FIG. 10.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

What is claimed is:

1. A mask for supplying gas under pressure to the nasal airway of a human, including:
   a series of flexible stretchable straps formed from an elastomeric material for locating the mask against a human face, the straps being integrally formed or joined to define a perimeter enclosing an aperture adapted to fit around a nasal area of a human, the straps being shaped and configured to approximate to a three dimensional shape of a region around the nasal area of a human face; and defining a face contacting portion having a non-face contacting side; and
   a manifold disposed on the non-face contacting side of the face contacting portion, the manifold including means for connection to a gas supply means;
   wherein stretching of the straps around the nasal area of the human causes the straps to mould to the contours of the nasal area of the face so that the straps form a seal around the nasal area which is a relatively tight fitting seal.

2. A mask as claimed in claim 1 wherein the aperture is generally triangular.

3. A mask as claimed in claim 1 further including a flexible sealing element extending along one inwardly facing side of each strap.

4. A mask as claimed in claim 3 wherein the sealing element is generally convex in cross-section.

5. A mask as claimed in claim 1 wherein three flexible arms extend away from the perimeter for securing the face-contacting portion to a human's head or face.

6. A mask as claimed in claim 5 wherein a pad is defined at the end of each flexible arm distal from the perimeter.

7. A mask as claimed in claim 6 wherein each pad defines slots.

8. A mask as claimed in claim 3 wherein the straps and sealing element are integrally moulded from an elastomeric material.

9. A mask as claimed in claim 1 wherein the thickness of the straps is from 2 to 4 mm.

10. A mask as claimed in claim 1 wherein a plurality of small holes having a diameter of up to 5 mm are defined on the manifold to provide a constant leak to atmosphere.

11. A mask as claimed in claim 5 wherein the manifold extends along one of the arms of the mask where a port for receiving a gas delivery pipe is provided.

12. A mask as claimed in claim 1 wherein the manifold is made of the same thin flexible elastomeric material that is used for the straps and wherein the material forming the manifold is 0.75 to 1.5 mm thick, preferably about 1 mm thick.

13. A mask as claimed in claim 1 wherein the manifold includes a plurality of large diameter holes.

14. A method of supplying a gas to the airway of a human using a mask as claimed in claim 1.

15. A mask as claimed claim 14 wherein three flexible arms extend away from the perimeter for attaching the mask to a harness.

16. A mask as claimed in claim 15 further including a flexible sealing element extending along one inwardly facing side of each strap.

17. A mask as claimed in claim 15 wherein the sealing element is generally convex in cross-section.

18. A mask as claimed in claim 16 wherein the manifold extends along one arm where a port or hole for receiving a gas delivery pipe is provided.

19. A harness for supplying gas under pressure to a nasal airway of a human, including:
   a series of flexible stretchable straps formed from an elastomeric material for locating the harness against a human face, the straps being integrally formed or joined to define a perimeter enclosing an aperture adapted to fit around a nasal area of a human, the straps being shaped and configured to approximate to a three dimensional shape of a region around a nasal area of a human face; and
   a means for supplying a flow of gas directed generally towards the perimeter of the harness including means for connection to a gas supply means;
   wherein stretching of the straps around the nasal area of the human causes the straps to mould to contours of the nasal area of a human face so that the straps anchor the harness to a human face relatively tightly.

20. A harness as claimed in claim 19 wherein the aperture is generally triangular.

21. A harness as claimed in claim 20 wherein a pad is defined at the end of each flexible arm distal from the perimeter.

22. A harness as claimed in claim 20 wherein a pipe extends along at least one of the arms, the pipe or pipes terminating in an open end adjacent the perimeter.

23. A harness as claimed in claim 19 wherein three flexible arms extend away from the perimeter.

24. A harness as claimed in claim 23 wherein each pad defines slots.

25. A harness as claimed in claim 19 wherein the straps and sealing element are integrally moulded from an elastomeric material.

26. A harness as claimed in claim 19 wherein the thickness of the straps is between 2 to 4 mm.

27. A mask for supplying gas under pressure to a nasal airway of a human, including:

a series of flexible stretchable straps formed from an elastomeric material for locating the mask against the human face, the straps being integrally formed or joined to define a perimeter enclosing a generally triangular aperture adapted to fit around a nasal area of a human, the straps being shaped and configured to approximate to a three dimensional shape of a region around a nasal area of a human face and to define a face contacting portion and a non-face contacting portion on an opposite side of the straps to the face contacting portion; and at least two flexible arms extending away from the perimeter wherein the arms and perimeter are integrally formed from an elastomeric material;

a manifold disposed on the non-face contacting side of the face contacting portion, the manifold including means for connection to a gas supply means wherein the manifold is also formed from the same elastomeric material as the straps;

wherein stretching of the straps around the nasal area of a human causes the straps to mould contours of the nasal area of the face so that the straps form a seal around the nasal area which is a relatively tight fitting seal.

\* \* \* \* \*